United States Patent [19]

Vanney et al.

[11] Patent Number: 5,713,952
[45] Date of Patent: Feb. 3, 1998

[54] APPARATUS FOR ATTACHMENT OF HEART VALVE HOLDER TO HEART VALVE PROSTHESIS

[75] Inventors: Guy P. Vanney, Blaine; Kurt D. Krueger, Stacy, both of Minn.

[73] Assignee: St. Jude Medical, Inc., St. Paul, Minn.

[21] Appl. No.: 526,854

[22] Filed: Sep. 11, 1995

[51] Int. Cl.$^6$ ............................................. A61F 2/24
[52] U.S. Cl. ....................................... 623/2; 623/900
[58] Field of Search ......................... 623/2, 900; 606/1; 206/438

[56] References Cited

U.S. PATENT DOCUMENTS

| | | | |
|---|---|---|---|
| 3,546,710 | 12/1970 | Shumakov et al. | 3/1 |
| 3,574,865 | 4/1971 | Hamaker | 3/1 |
| 3,828,787 | 8/1974 | Anderson et al. | 623/2 |
| 3,860,005 | 1/1975 | Anderson et al. | 128/303 |
| 4,655,218 | 4/1987 | Kulik et al. | 128/321 |
| 4,679,556 | 7/1987 | Lubock et al. | 128/303 |
| 4,683,883 | 8/1987 | Martin | 128/303 |
| 4,755,181 | 7/1988 | Igoe | 623/2 |
| 4,865,600 | 9/1989 | Carpentier et al. | 623/2 |
| 4,932,965 | 6/1990 | Phillips | 623/2 |
| 5,071,431 | 12/1991 | Sauter et al. | 623/2 |
| 5,163,954 | 11/1992 | Curcio et al. | 623/2 |
| 5,236,450 | 8/1993 | Scott | 623/2 |
| 5,370,685 | 12/1994 | Stevens | 623/2 |
| 5,403,305 | 4/1995 | Sauter et al. | 623/2 |
| 5,425,705 | 6/1995 | Evard et al. | 604/28 |
| 5,433,700 | 7/1995 | Peters | 604/4 |

FOREIGN PATENT DOCUMENTS

| | | |
|---|---|---|
| 2 198 726 | 4/1974 | France . |
| 1690738 A1 | 11/1991 | U.S.S.R. . |
| WO 94/18881 | 9/1994 | WIPO . |
| WO 95/15715 | 6/1995 | WIPO . |
| WO 95/17139 | 6/1995 | WIPO . |

*Primary Examiner*—Randy C. Shay
*Attorney, Agent, or Firm*—Hallie A. Finucane, Esq.

[57] ABSTRACT

A holder for engaging a heart valve prosthesis during implantation includes a mechanism for attaching the holder to the heart valve prosthesis. The heart valve prosthesis includes a circular valve body having an annulus with a substantially annular aperture therein. At least one movable occluder is carried in the aperture and is movable between an open position and a closed position. The attachment mechanism attaches to the occluder thereby securing the holder to the heart valve prosthesis.

3 Claims, 6 Drawing Sheets

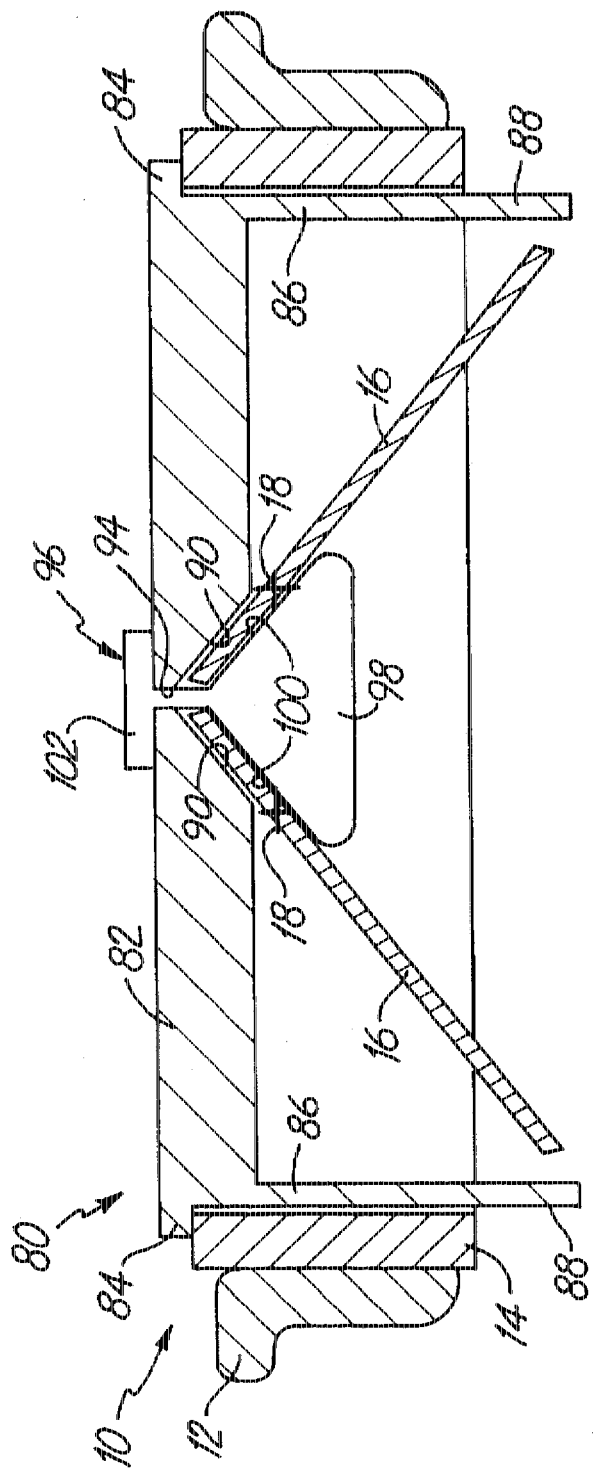

APPARATUS FOR ATTACHMENT OF HEART VALVE HOLDER TO HEART VALVE PROSTHESIS

The present invention relates to devices for implanting heart prostheses. More specifically, the invention relates to attachment of a heart valve holder to a heart valve prosthesis.

BACKGROUND OF THE INVENTION

Holders for holding heart valve prostheses during implantation are known. They are used for positioning, holding, supporting and presenting the valve during surgery. U.S. Pat. No. 3,828,787, issued Aug. 13, 1974, to Anderson et al., entitled COLLET FOR HOLDING HEART VALVE, shows a heart valve holder carried on a distal end of an elongated handle. U.S. Pat. No. 4,932,965, issued Jun. 12, 1990, to Phillips, entitled ARTIFICIAL VALVE, AND NEEDLE AND SUTURE HOLDER AND METHOD OF USING SAME, shows another heart valve holder in which the valve is held against distal ends of a pair of elongated legs during implantation.

Typically, heart valve replacement surgery is an involved procedure in which a sternotomy or thoracotomy is performed and the chest cavity of the patient must be widely opened to provide access to the patient's heart. This provides a surgeon with direct, unobstructed access to the heart. However, this procedure requires a prolonged period to recover from the trauma suffered to the upper torso.

Recently, a procedure has been developed wherein open heart surgery is performed through trocars placed in small incisions between ribs of the patient. This is described in International Publication No. WO 95/15715, entitled DEVICES AND METHODS FOR INTRACARDIAC PROCEDURES; U.S. Pat. No. 5,433,700, issued Jul. 18, 1995, to Peters, entitled METHOD FOR INTRALUMINALLY INDUCING CARDIOPLEGIC ARREST AND CATHETER FOR USE THEREIN; U.S. Pat. No. 5,425,705, issued Jun. 20, 1995, to Evard et al., entitled THORACOSCOPIC DEVICES AND METHODS FOR ARRESTING THE HEART; and International Publication No. WO 94/18881, entitled METHOD FOR PERFORMING THORASCOPIC CARDIAC BYPASS PROCEDURES. In this procedure, elongated tools are used to operate on the heart through the trocars. As discussed in Publication No. WO 95/15715, this procedure can be used during heart valve replacement. When a heart valve prosthesis is inserted through a trocar, extreme care has to be taken for protecting the occluders in the valve, and once inserted, it becomes desirable to change the orientation of the valve prior to implantation to simplify the suturing of the heart valve prosthesis in place.

The trocar results in minimal rib spreading and does not involve the significant chest trauma associated with traditional open heart surgery. One advantage of this procedure is that the recovery period can be reduced significantly. Unfortunately, mechanical heart valves and the associated assembly used for implantation are large relative to the intercostal space between the ribs and are difficult to fit therethrough. Further, the heart valve holder must be securely attached to the heart valve prosthesis and yet be easily removed once the valve has been attached to the heart tissue annulus.

SUMMARY OF THE INVENTION

A device for engaging a heart valve prosthesis during implantation includes a mechanism for attaching the device to the heart valve prosthesis. The heart valve prosthesis includes a circular valve body having an annulus with a substantially annular aperture therein. At least one movable occluder is carried in the annulus and is movable between an open position and a closed position. The attachment mechanism includes a member which engages to the occluder(s), thereby affixing the device to the valve prosthesis at the occluder(s). The member is selectively removable from the occluder(s) thereby releasing the device from the occluder(s). In one embodiment, an elongated handle couples to the device and extends away from the device in a plane generally parallel with a plane formed by the annulus of the heart valve prosthesis.

In one embodiment, the attachment mechanism is disengaged by withdrawing the attachment mechanism from the occluder. This may be by directly pulling on the attachment mechanism or by actuating a withdrawal apparatus.

BRIEF DESCRIPTION OF THE DRAWINGS

FIG. 3 is a cross sectional view of a heart valve holder in accordance with another embodiment engaged with a heart valve prosthesis.

DETAILED DESCRIPTION OF THE PREFERRED EMBODIMENTS

The invention relates to attachment of a prosthetic heart valve holder to a heart valve prosthesis. The holder is used to position the heart valve prosthesis during implantation. In one embodiment, this implantation is through minimally invasive surgery such as when performed through a small trocar. The holder and valve are carried at the distal end of a handle which extends perpendicular to the axis of the valve annulus during insertion through the trocar. Reference is made to copending application Ser. No. 08/526,530 filed on even date herewith entitled LOW PROFILE MANIPULATORS FOR HEART VALVE PROSTHESES. For purposes of this description of the invention, the holder and attachment mechanism will be described generally with regard to its use. The holder and attachment mechanism may be used with any appropriate heart valve prosthesis including heart valve prostheses which are available from St. Jude Medical, Inc., of St. Paul, Minn.; Baxter Healthcare Corp., Edwards CVS Div., Irvine, Calif.; Medtronic, Inc., Minneapolis, Minn.; Shiley, Inc., Irving, Calif.; Omniscience Medical Inc., Grove Heights, Minn.; Carbomedics, Inc., Austin, Tex.; and Sorin Biomedica, Saluggia, Italy. In general, heart valve prostheses depicted herein are shown in a generic form and the scope of the present invention is intended to cover variations required to adapt the holder and attachment mechanism to different heart valve prostheses.

Figure 1A:
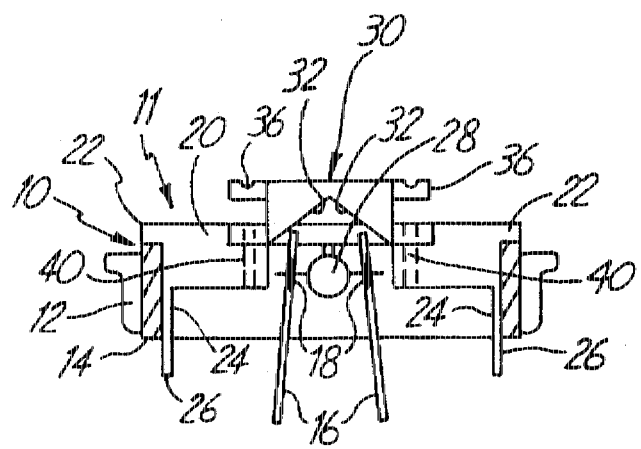
FIG. 1A is a cross sectional view of a heart valve prosthesis adjacent a holder in accordance with one embodiment.
Figure 1B:
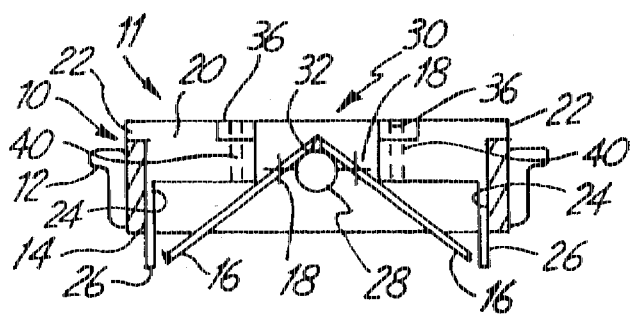
FIG. 1B is a cross sectional view of the holder and heart valve prosthesis of FIG. 1A showing a holder engaged with the heart valve prosthesis.

FIG. 1A is a cross sectional view of heart valve prosthesis 10 and heart valve holder 11 in accordance with one embodiment of the present invention. Prosthesis 10 includes suture cuff 12 and heart valve prosthesis body 14. Body 14 forms an annulus for allowing blood flow therethrough. Occluders 16 are positioned in the heart valve prosthesis body 14 and are movable between an open position as shown in FIG. 1A to a closed position as shown in FIG. 1B. Occluder(s) 16 rotate about pivots 18. Although the particular heart valve prosthesis 10 has been shown in accordance with one embodiment, other heart valves may also be used with the present invention. For example, the heart valve prosthesis may include different numbers of occluders including a single occluder, may have a different orifice or annulus shape, or the occluders may operate in accordance with a different mechanism.

Heart valve prosthesis holder 11 includes a top member 20 having lip portion 22 which engages the top rim of heart valve prosthesis body 14. Holder 11 includes interior extensions 24 which provides a surface adapted to engage the interior surface of heart valve prosthesis body 14. Distal ends 26 protrude beyond the bottom rim of heart valve prosthesis body 14 and occluder(s) 16. Holder 11 includes capture rod 28 which is positioned between occluder(s) 16, and in the embodiment of FIGS. 1A--1C, is aligned between pivots 18. In FIG. 1A, a capture block 30 of holder 11 is shown in an open or released position. Capture block 30 includes occluder engaging surfaces 32 adapted to conform to the surfaces of occluders 16 and maintain occluders 16 in the partially closed position shown in FIG. 1B. FIG. 1B shows capture block 30 moved in a closed position downward relative to top member 20 such that occluder engaging surfaces 32 engage occluders 16 in the partially closed position. This causes the occluder(s) 16 to be captured between capture rod 28 and occluder engaging surfaces 32 of capture block 30. Capture block 30 includes suture flanges 36.

Figure 1C:
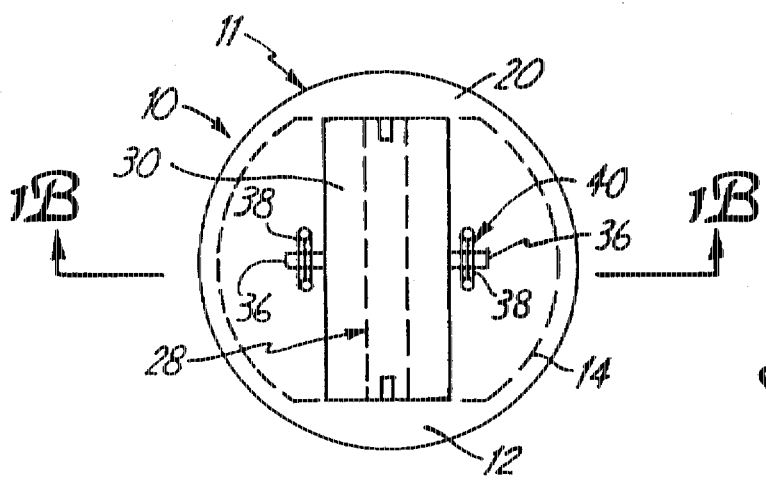
FIG. 1C is a top plan view of the holder of FIG. 1B in the engaged position.

FIG. 1C is a top plan view of holder 11 showing sutures 38 which secure capture block 30 to top member 20 by extending around suture lips 36 through suture holes 40.

In operation, heart valve prosthesis 10 is held by heart valve holder 11 as shown in FIGS. 1B and 1C at occluders 16. Occluders 16 are maintained in a partially or fully closed position and are protected from damage by distal portions 26 of heart valve prosthesis body 14 during implantation. In this position, a surgeon attaches heart valve prosthesis 10 to the tissue annulus formed by excision of the natural heart valve from a patient. Suture cuff 12 is sutured to the heart tissue annulus by techniques known in the art. Following attachment of heart valve 10 to the tissue annulus, heart valve holder 11 may be removed by cutting sutures 38 and moving capture block 30 to the open position shown in FIG. 1A. Removal and manipulation of holder 11 may be with an elongated handle (not shown). This frees occluder(s) 16 such that holder 11 may be removed from prosthesis 10.

Figure 2:
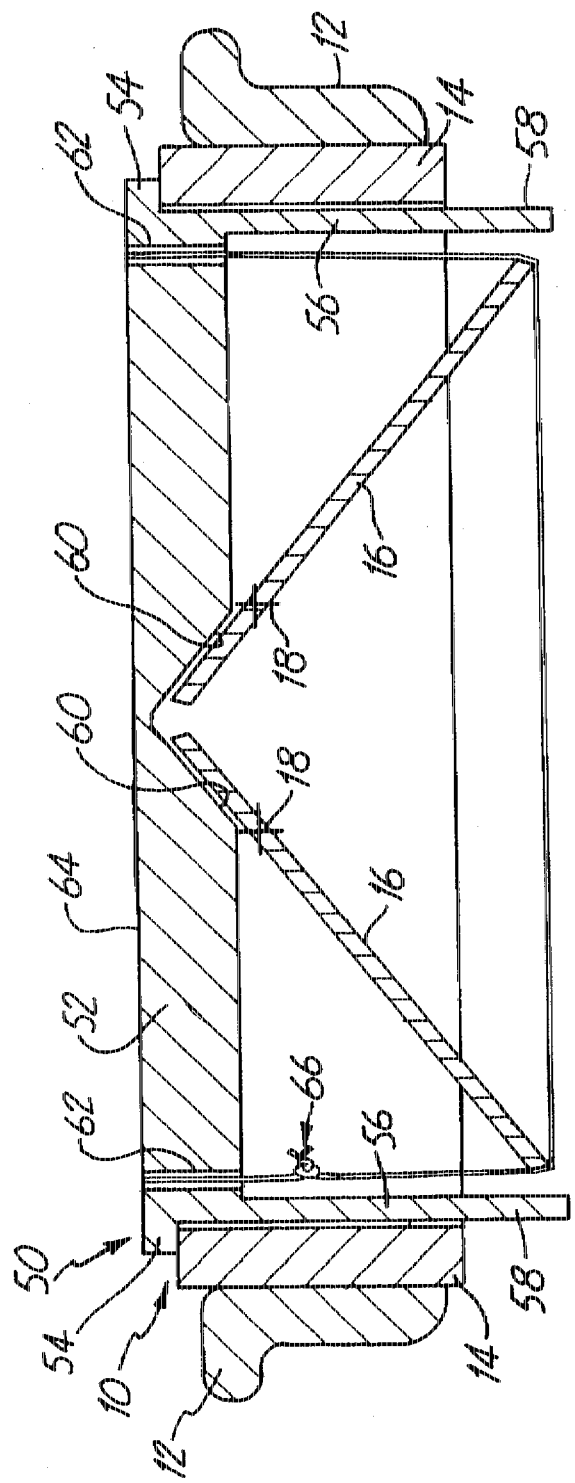
FIG. 2 is a cross sectional view of a heart valve holder in accordance with another embodiment engaged with a heart valve prosthesis.

FIG. 2 is a cross sectional view of heart valve holder 50 in accordance with another embodiment engaged with heart valve prosthesis 10. Heart valve holder 50 includes top member 52 having lip portion 54 adapted for engagement with the top rim of heart valve prosthesis body 14. Holder 50 includes interior extensions 56 which conform to the interior surface of heart valve prosthesis body 14 and distal extensions 58 which extend beyond the lower rim of heart valve prosthesis body 14 and occluder(s) 16. Top member 52 includes occluder conforming surfaces 60 which are adapted to conform to occluders 16 when holder 50 is engaged with heart valve prosthesis 10 as shown in FIG. 2. Top member 52 includes suture holes 62 adapted for receiving a suture 64. Suture 64 extends around top member 52, through suture holes 62 and around occluders 16, thereby securing holder 50 to heart valve prosthesis 10. Suture 64 is secured with knot 66. Holder 50 is held against prosthesis 10 at occluder conforming surfaces 60 and lip portion 54 due to the pressure applied on occluders 16 by suture 64. Distal extensions 58 protect occluders 16 from damage during implantation. Following implantation of heart valve prosthesis 10, holder 50 may be removed by cutting suture 64 and disengaging holder 50 from heart valve prosthesis 10. Although only a single suture 64 is shown, multiple sutures may also be used.

FIG. 3 is a cross sectional view of heart valve prosthesis holder 80 in accordance with another embodiment engaged with heart valve prosthesis. Holder 80 includes top member 82 and lip portion 84. An interior extension 86 generally conforms to the interior surface of heart valve prosthesis body 14. Distal extensions 88 extend beyond the bottom of heart valve prosthesis body 14. Top member 82 includes occluder conforming surfaces 90 adapted to conform to occluders 16, as shown in FIG. 3. Top member 82 includes opening 94 adapted to receive locking key 96. Locking key 96 includes interior locking portion or member 98 having occluder engaging surfaces 100 and handle 102.

Holder 80 is held to prosthesis 10 between conforming surfaces 90 of top member 82 and engaging surfaces 100 of locking key 96. Following insertion and attachment of heart valve prosthesis 10 to the heart tissue annulus of a patient, holder 80 is removed by rotating locking key 96 ninety degrees about the axis of prosthesis 10 such that occluders 16 are freed from occluder engaging surfaces 100. In this position, occluder(s) 16 are disengaged. Thus, prosthesis holder 80 may be removed from valve prosthesis 10. Alternatively, member 98 may be removed from valve holder 80 through opening 94 in top member 82. Holder 80 may then be removed from prosthesis 10. Distal extensions 88 protect occluders 16 during implantation. Variations on this embodiment include changing the position or length of the engaging surface 100 and conforming surface 90. Another variation would be insertion of a key member(s) adjacent to, but not between, occluder(s) 16, which engage distal ends of occluder(s) 16 such that interior extension 86 would not be required.

Alternatively, holder 80 may be held to prosthesis 10 between lip portion 84 and engaging surface 100 of locking key 96.

Figure 4B:
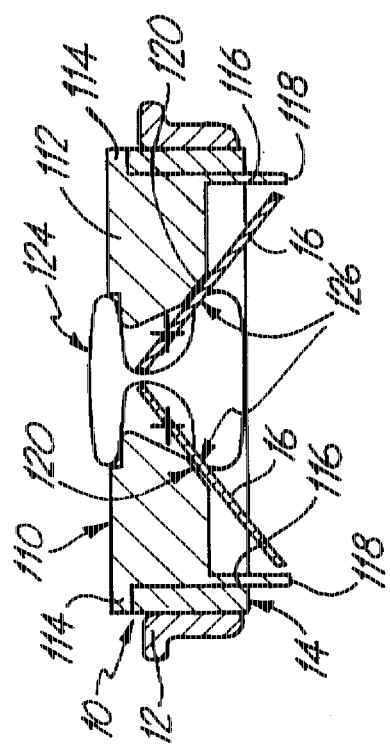
FIG. 4B is a cross sectional view of a holder of FIG. 4A engaged with the heart valve prosthesis.
Figure 4A:
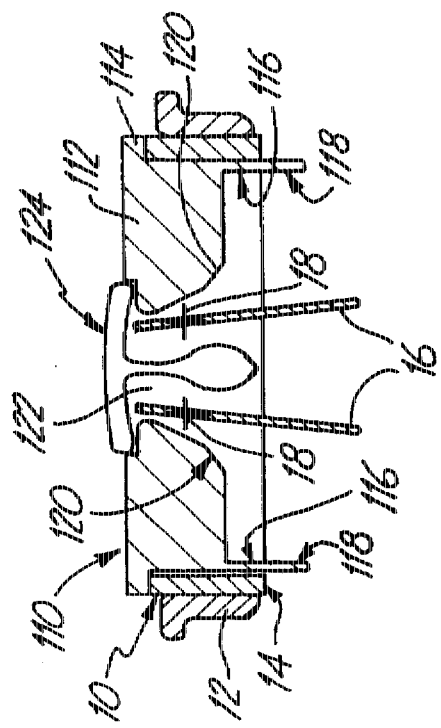
FIG. 4A is a cross sectional view showing a holder in accordance with another embodiment adjacent a heart valve prosthesis.

FIG. 4A is a cross sectional view of a heart valve prosthesis holder 110 in accordance with another embodiment. Holder 110 includes top member 112 having lip portion 114 adapted for engaging heart valve prosthesis body 14. Interior extensions 116 conform to the interior surface of heart valve prosthesis body 14 and connect to distal extensions 118 which extend beyond the bottom rim of heart valve prosthesis body 14. Top member 112 includes occluder conforming surfaces 120 adapted for engaging occluders 16. Opening 122 in top member 112 receives inflatable element 124. Inflatable element 124 is shown in a deflated condition in FIG. 4A and in an inflated condition in FIG. 4B. In an inflated condition, inflatable element 124 provides occluder engaging surfaces 126 such that occluders 16 are captured between engaging surfaces 126 and conforming 120, thereby securing holder 110 to heart valve prosthesis 10. Support is also provided by lip portion 114. Distal extensions 118 protect occluders 16 during implantation. Following attachment of heart valve prosthesis 10 to the heart tissue annulus, holder 110 is removed by deflating inflatable element 124 such that holder 110 may be lifted from prosthesis 10. An elongated control coupling may be provided to element 124 to selectively, remotely deflate element 124.

Alternatively, valve prosthesis 10 is captured between engaging surface 126 and lip portion 114 of holder body 110.

Figure 5A:
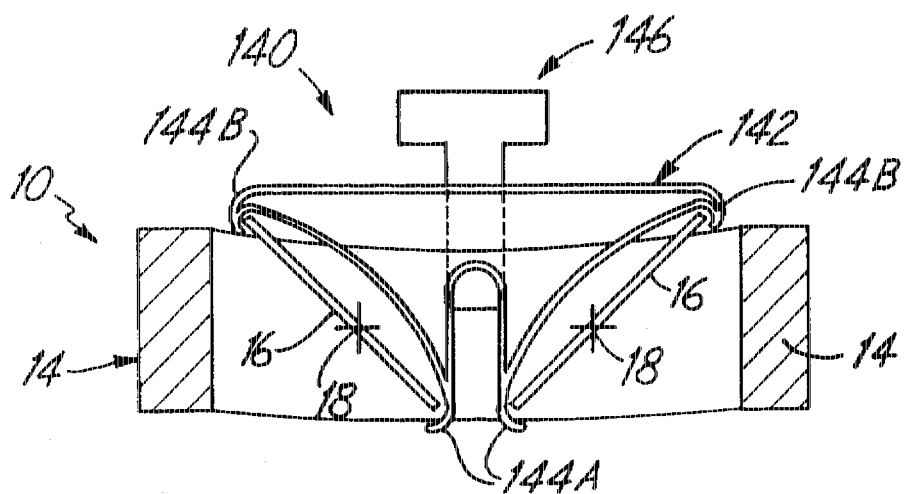
FIG. 5A is a cross sectional view of a holder in accordance with another embodiment adjacent a heart valve prosthesis.

FIG. 5A is a cross sectional view of a holder 140 in accordance with another embodiment adjacent heart valve prosthesis 10. Prosthesis 10 is shown in simplified form having body 14, occluders 16 and pivots 18. Holder 140 includes gripper 142 having attachment mechanisms 144A and 144B which extend around edges of occluders 16. A plunger 146 extends through an opening in gripper 142 and is shown in a withdrawn position in FIG. 5A.

Figure 5B:
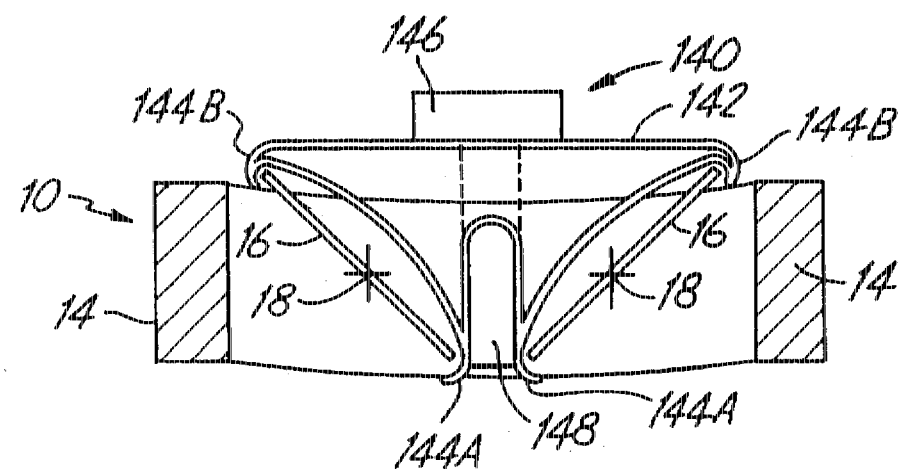
FIG. 5B is a cross sectional view of the holder of FIG. 5A engaged with the heart valve prosthesis.

In FIG. 5B, tip portion 148 of plunger 146 causes attachment mechanisms 144A to spread apart thereby locking gripper 142 to occluders 16. In the embodiment of holder 140 in FIGS. 5A and 5B, a control coupling mechanism (not shown) may be provided to control operation of plunger 146 from a remote location. Similarly, such a control mechanism may be used in the other embodiments set forth herein.

Figure 6A:
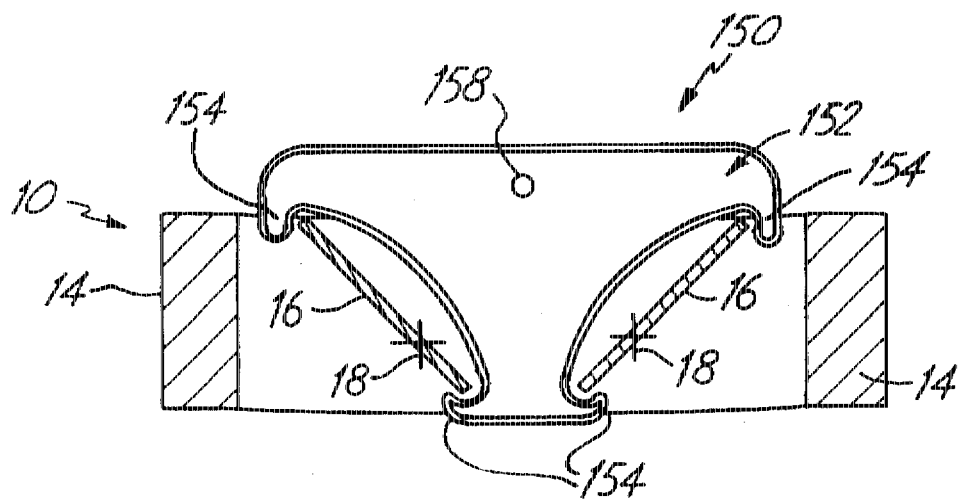
FIG. 6A is a cross sectional view of a holder in accordance with another embodiment engaged with the heart valve prosthesis.

FIG. 6A is a cross sectional view of holder 150 in accordance with another embodiment engaged with heart valve prosthesis 10. Holder 150 in FIG. 6A is similar to holder 140 of FIGS. 5A and 5B. Holder 150 includes body 152 having engagement mechanisms 154 which engaged edges of occluders 16.

Figure 6B:
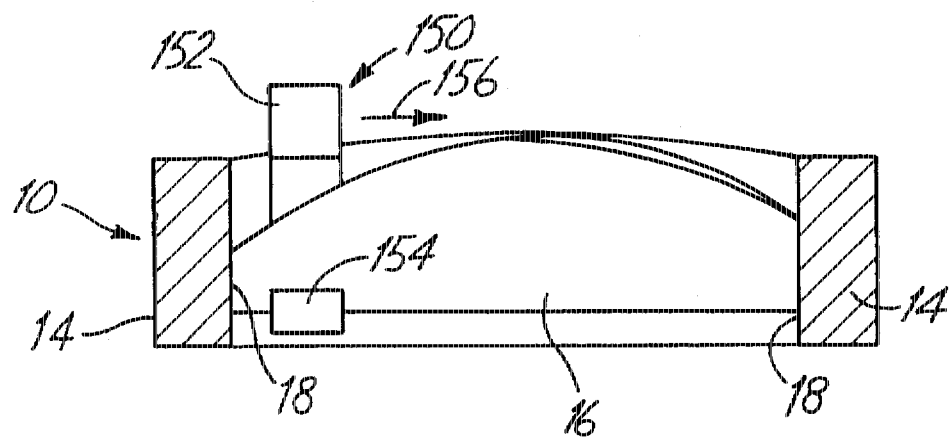
FIG. 6B is a cross sectional view of the holder and heart valve prosthesis of FIG. 6A.

FIG. 6B is a cross sectional view of holder 150 in heart valve prosthesis 10. FIG. 6B is a cross sectional view with valve 10 in holder 150 rotated ninety degrees about the axis of valve 10 in FIG. 6A. FIG. 6B shows holder 150 offset from the center axis of valve 10 such that holder 150 is disengaged from valve 10. Holder 150 may be positioned to engage occluders 16 by moving holder 150 in the direction indicated by arrow 156 in FIG. 6B. Holder 150 includes suture hole 158 shown in FIG. 6A which is capable of receiving a suture (not shown) to secure holder 150 in an engaged position with occluders 16.

As used herein, attachment mechanism is used to mean a mechanism for attaching to the occluder. The preferred embodiments set forth a number of attachment mechanisms. However, the term "attachment mechanism" is intended to describe any other mechanism for attaching a valve to an occluder which is within the scope of the invention.

It should be understood that the present invention extends to any variation or embodiment which would be apparent to those skilled in the art. The concepts set forth herein are applicable to any appropriate valve configuration for both aortic and mitral implantation.

Typically, the holders described herein are attached to an elongated handle such that a surgeon may manipulate the heart valve using the proximal end of the handle during implantation.

Although the present invention has been described with reference to preferred embodiments, workers skilled in the art will recognize that changes may be made in form and detail without departing from the spirit and scope of the invention.

What is claimed is:

1. An apparatus for holding a heart valve prosthesis and providing a low profile during implantation, the heart valve prosthesis including a heart valve prosthesis body and a movable occluder having a first occluder surface and a second occluder surface opposite the first occluder surface, the apparatus comprising:

a top member sized to fit proximate an annulus of the heart valve prosthesis;

a lip portion coupled to the top member adapted for abutting the annulus of the heart valve prosthesis;

an interior extension coupled to the top member extending through heart valve prosthesis body and generally conforming to an interior portion of the prosthesis body;

a distal extension coupled to the interior extension extending beyond the heart valve prosthesis body opposite the top member to protect the movable occluder;

a conforming surface in the top member shaped to conform to the first occluder surface to maintain the first occluder surface in a substantially closed position when the top member and lip portion engage the prosthesis body; and a suture extending around the top member and adapted to extend around the movable occluder, thereby coupling the top member to the heart valve prosthesis body and the conforming surface to the fist occluder surface and maintaining the movable occluder in the substantially closed position whereby the occluder is protected from damage by the heart valve prosthesis body and the distal extension.

2. The apparatus of claim 1 including a second conforming surface adapted to conform to a first surface of a second movable occluder of the heart valve prosthesis to maintain the second movable occluder in a substantially closed position.

3. The apparatus of claim 1 wherein the top member includes a suture hole formed therein for receiving the suture.

* * * * *